United States Patent [19]

Brudny

[11] 4,417,569
[45] Nov. 29, 1983

[54] UNIVERSAL FUNCTIONAL SHOULDER ORTHOSIS

[75] Inventor: Joseph Brudny, New York, N.Y.

[73] Assignee: Alexander Mencher, Forest Hills, N.Y.

[21] Appl. No.: 312,228

[22] Filed: Oct. 19, 1981

[51] Int. Cl.³ ............................ A61F 3/00; A61F 5/01
[52] U.S. Cl. ........................................ 128/77; 128/88
[58] Field of Search ...................... 3/1, 12; 128/77, 78, 128/82, 83, 85, 87 R, 88, 89 R, 94

[56] References Cited

U.S. PATENT DOCUMENTS

| 1,257,297 | 2/1918 | Brown | 128/94 X |
| 1,340,630 | 5/1920 | Maddox | 128/88 UX |
| 1,639,815 | 8/1927 | Siebrandt | 128/88 |
| 1,653,601 | 12/1927 | Foulke | 128/88 |
| 2,191,283 | 2/1940 | Longfellow | 128/88 |
| 2,859,746 | 11/1958 | Roberson | 128/87 R |
| 4,013,070 | 3/1977 | Harroff | 128/77 X |

Primary Examiner—Ronald Frinks
Attorney, Agent, or Firm—Alexander Mencher

[57] ABSTRACT

An orthotic device attached to the external part of the body is adapted to provide support for the malfunctioning arm of a patient, said support offering a variety of stable arm positions in space in a manner essential for functional use of the forearm and hand. A plate attached to the body anchors an artificial ball and socket joint. The joint is actuated by a lockable rod which carries an adjustable elbow support or trough. Such structure provides the adequate range of motion and the needed accompanying stabilization of the arm in space, while said ball and socket joint replaces and/or augments the human shoulder joint. The device is worn by the patient inconspicuously under a garment, is useful either during mobility, while seated or when recumbent, and is applicable to human beings whose willful control of the shoulder joint is absent or decreased as the result of illness or injury.

10 Claims, 12 Drawing Figures

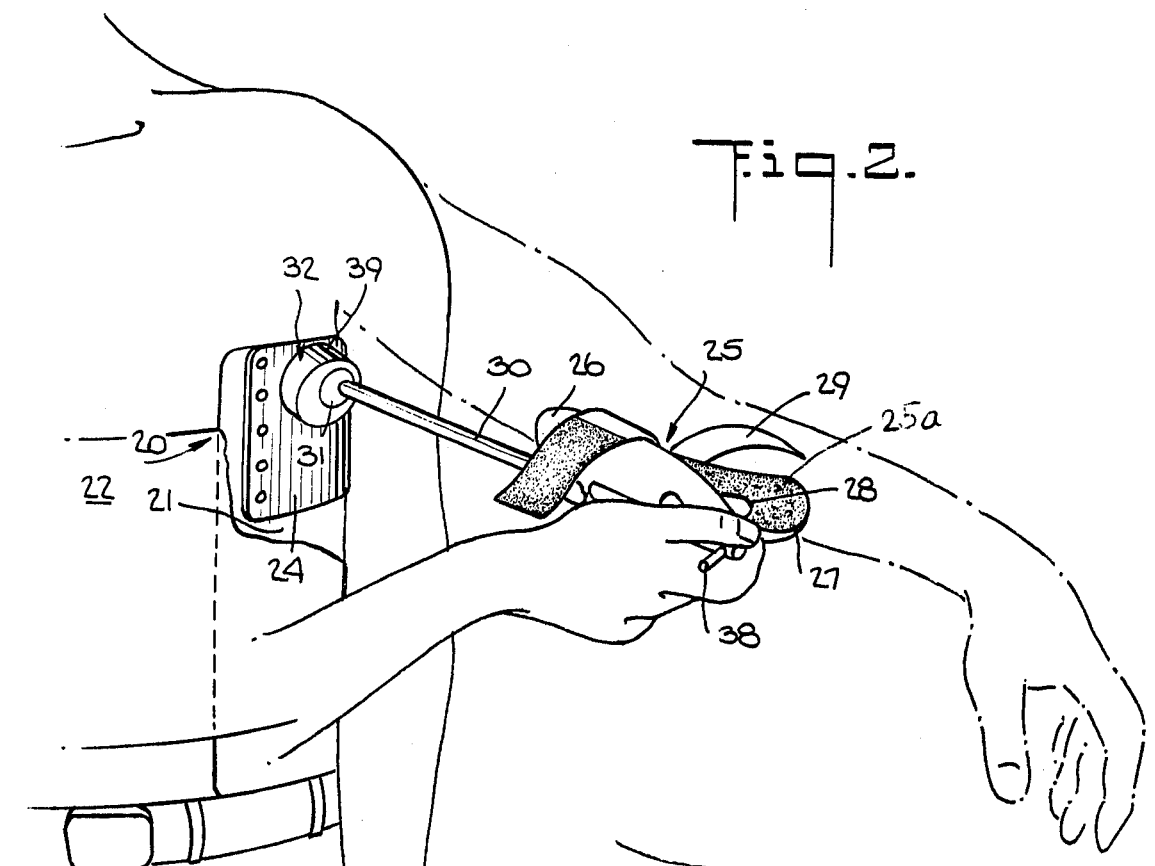
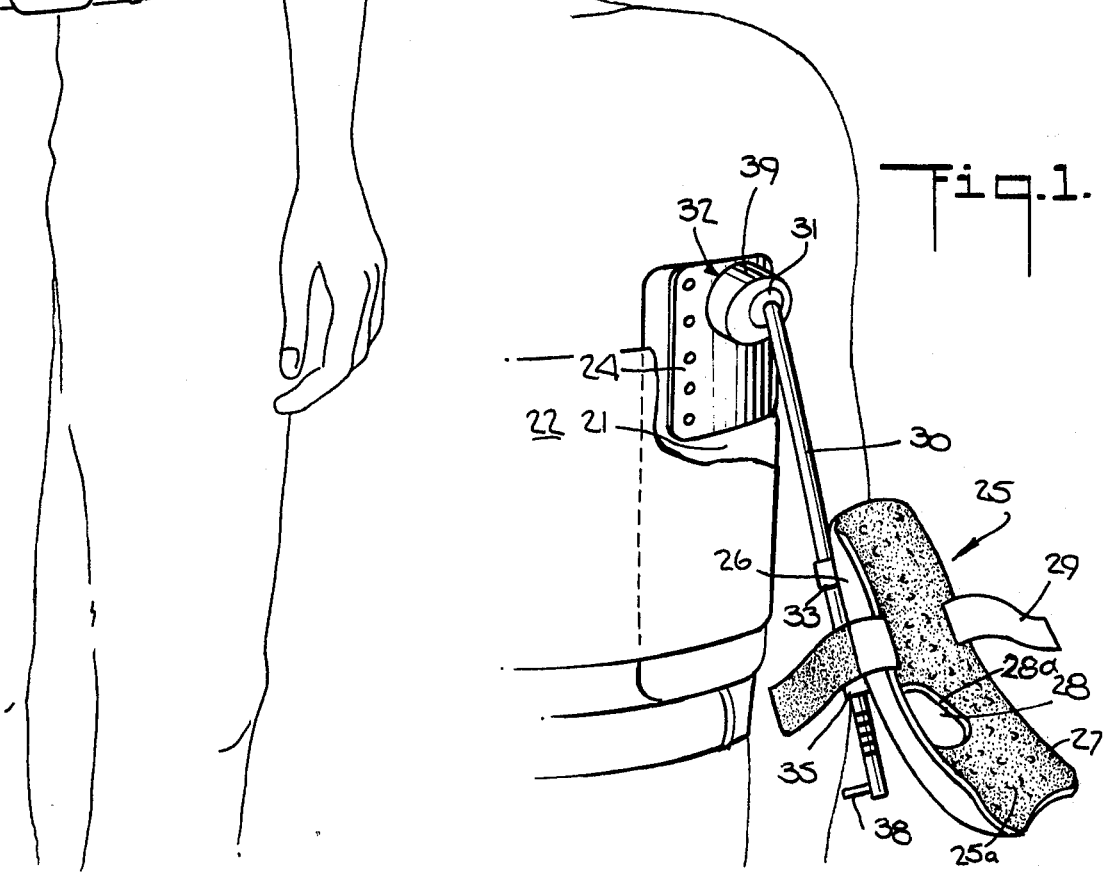

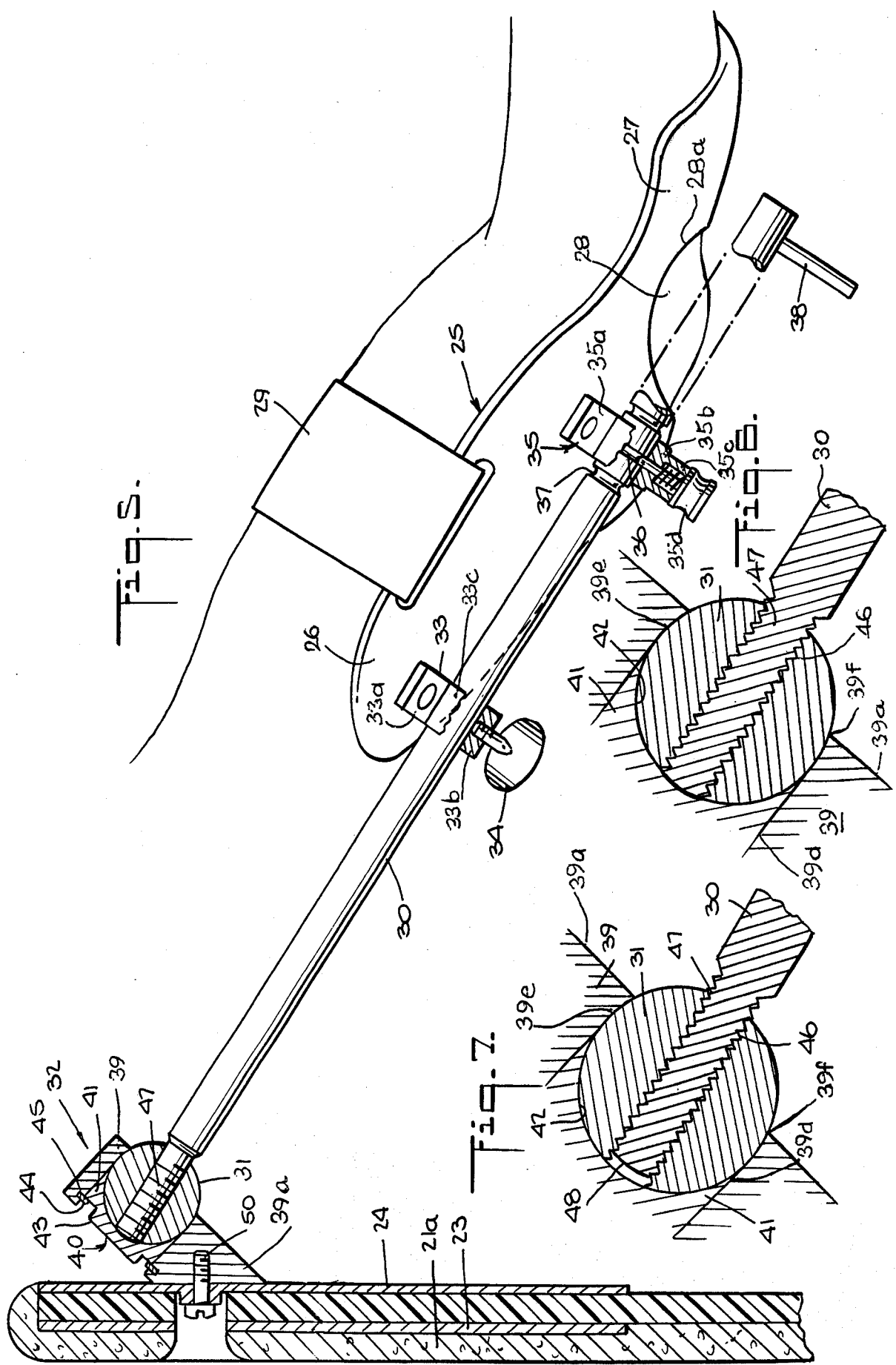

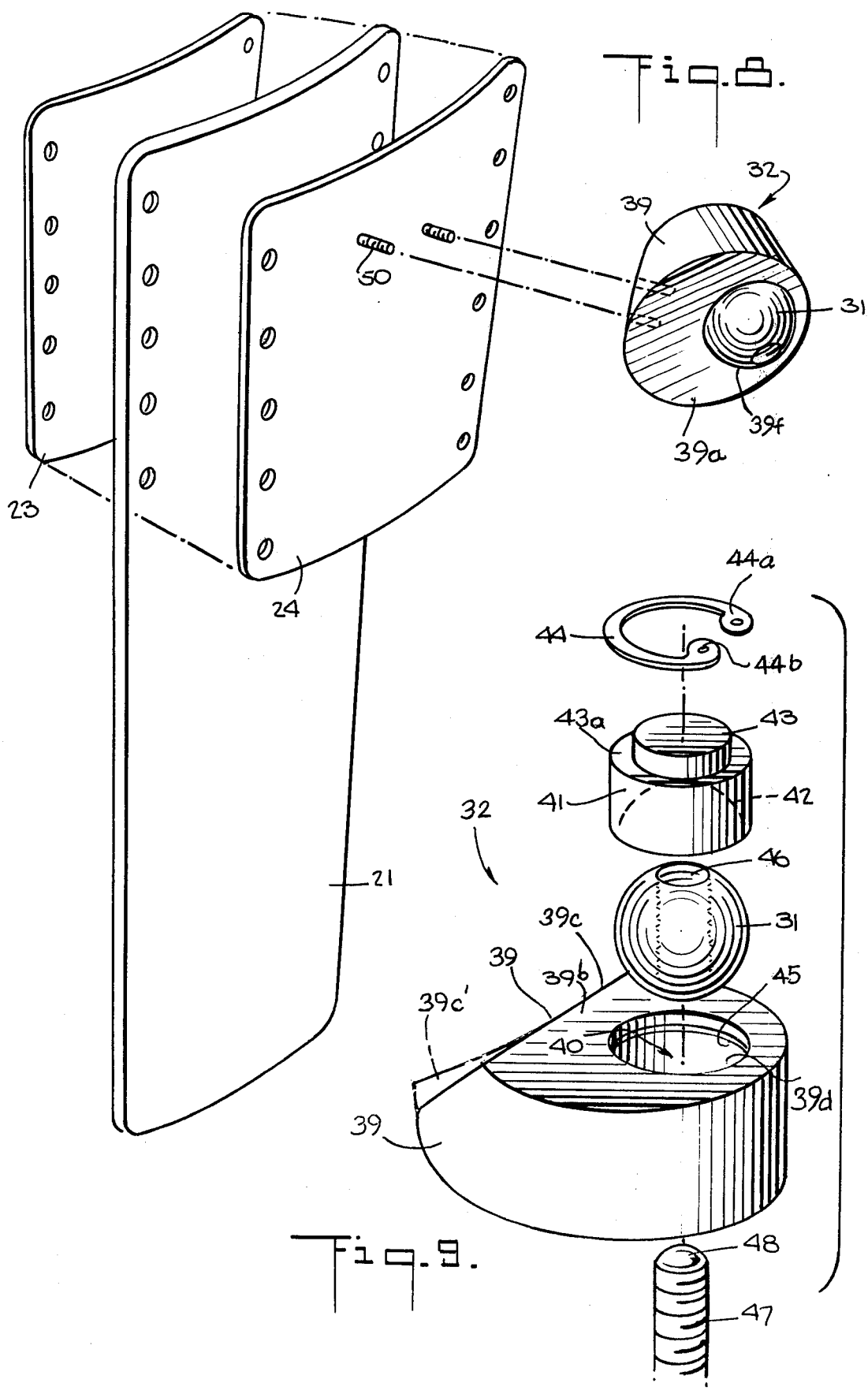

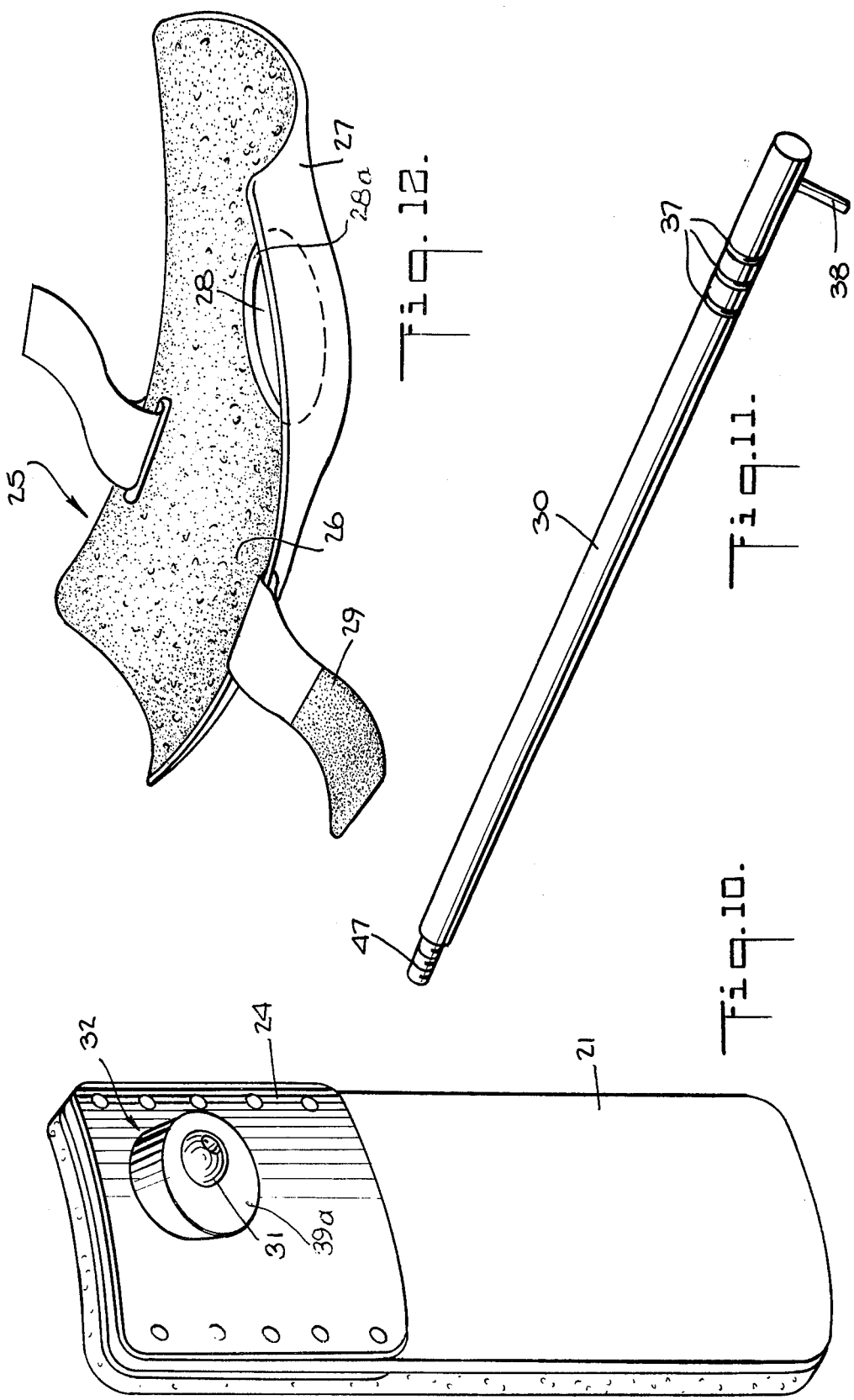

UNIVERSAL FUNCTIONAL SHOULDER ORTHOSIS

BACKGROUND OF THE INVENTION

The invention relates generally to orthotic devices applied to or attached to the external surface or part of the human body in order to improve function.

More specifically, the invention embraces an orthotic device of minimum parts and capable of replacing the basic function of the human shoulder joint by efficiently providing simultaneously stability as well as mobility of the arm. Such replacement is needed when illness or injury renders the shoulder joint nonfunctional. The device is worn in an inconspicuous manner both during mobility and rest thereby making it universally applicable for the purpose of increasing the function of the human upper limb when it is limited by illness or injury.

Prior orthotic devices for providing stability of the human arm at the shoulder joint include those known as hemiplegic shoulder slings and as airplane splints. The shoulder sling provides only questionable support to the arm and forearm, is known to limit the use of the hand, and is considered to have no appreciable effect on ultimate range of motion, or on pain and subluxation of the shoulder occurring despite its use. The airplane splint immobilizes the arm in a constant position, can be used for only short periods of time because of considerable pressure on the pelvic bone, and is a limiting factor in mobility.

Prior orthotic devices for providing mobility of the human arm at the shoulder joint include those primarily known as mobile arm supports and functional arm braces. The mobile arm supports (also known as ball-bearing forearm orthoses) are attached to a wheelchair and are thus suitable for the non-ambulatory patient only. The functional arm braces allow only certain motions at the flail shoulder but fail to provide sufficient stability and mobility when spasticity is a factor.

Prior art patents such as U.S. Pat. No. 1,340,630 issued to R. D. Maddox on May 18, 1920 and U.S. Pat. No. 2,859,746 issued to W. V. Roberson on Nov. 11, 1958 fail both in structure and purpose to attain the ends of the instant invention. Maddox shows a complexity of joints and connections of metallic rods with body, arm and forearm pads all adapted to retain the arm of the patient in any desired position relatively to the body during treatment for fracture and other injuries especially of the arm and shoulder. Roberson utilizes a ball-shaped pad and means for holding the pad in the armpit under pressure to support the shoulder joint of a dislocated shoulder and to enable the person to move his or her arm.

In summary, the various presently applicable orthotic devices do not satisfy as does the invention herein the need for a universal orthotic device capable of providing simultaneously stability and mobility at the shoulder joint, applicable both during ambulation and in a stationary position, and having the structural characteristics of an artificial ball and socket joint anchored to a body plate and operable by a lockable joint-actuating rod carrying an elbow support or trough connected to the rod.

The basic function of the human shoulder joint is to locate the arm in such a position that the use of the forearm, wrist and hand becomes functional during activities of daily living. This complex coordinated function is provided by simultaneous patterned movements of two muscle groups: extrinsic and intrinsic. The function of these muscles is a continuously coordinated task in which the intrinsic muscles anchor the humoral head in the glenoid fossa, thus providing stability for the arm, while the extrinsic muscles provide the dynamic forces needed to move the arm against gravity or resistance. The human shoulder joint is incongruous by nature, which means that the concave and convex surfaces are symmetrical. The concave surface is elongated and the convex surface is more circular thereby making the distance between them variable at each point during movement. For the human shoulder to provide stability and mobility, the simultaneous interaction of both intrinsic and extrinsic muscle groups is essential for function.

There are a number of clinical entities wherein the complex coordination of intrinsic and extrinsic muscle groups are absent or deficient. These occur as the result of illness or injury to the central nervous system, to the peripheral nervous system, as well as to the muscles and bony structures controlling and comprising the shoulder joint.

Lesions of the central nervous system such as the brain and the spinal cord cause imbalance between previously coordinated patterned movements with sequential facilitation or inhibition of certain intrinsic or extrinsic muscles of the shoulder joint. This imbalance renders certain muscles paretic or poorly responsive to volitional attempt at contraction, while other muscles become spastic, or showing excessive, uncontrollable and prolonged contraction. As the result of coexisting spasticity and paresis (e.g. in hemiplegia), an attempt at voluntary movement at the shoulder usually produces a stereotyped, abnormal and nonfunctional response. This pathological response at the shoulder limits or prevents any functional use of the forearm and hand which could otherwise be at times utilized meaningfully.

Lesions of the peripheral nervous system, such as the brachial plexus or its branches, may render certain muscles of the shoulder paretic, thus preventing stability and mobility of the shoulder joint. Such involvement prevents the functional use of the forearm and hand, the muscles of which may remain sufficiently innervated.

Diseases affecting shoulder girdle muscles, such as muscular dystrophy, also deprive the shoulder from stability and mobility with the resulting loss of function of the forearm and hand which may often be preserved.

Disease or injuries to the bony capsular and/or tendinous elements of the shoulder joint usually result in pain that limits its mobility and stability with consequent decrease or loss of function of the forearm and hand, such as the shoulder hand syndrome, or with involvement of the sympathetic nervous system such as the reflex sympathetic dystrophy syndrome.

SUMMARY AND OBJECTS OF THE INVENTION

The present disclosure embraces a novel orthotic device and a novel method for replacing and/or augmenting the normal function of the human shoulder joint when its stability and mobility are impaired or absent as the result of illness or injury, and at the same time enabling full flexion of the elbow and full supination, pronation and functional extension of the forearm.

It is among the principal objects of the invention involving novelty in both structure and method to provide a functioning ball and socket joint performing in a manner paralleling the function of the human shoulder joint and adapted to be interposed between the arm and the lateral aspects of the chest, and having external means and a minimum number of parts and steps to control the stability and mobility of the human arm.

Another object of the invention resides in the means for selecting a variety of stable positions of the human arm in space which allows functional use of the forearm and hand.

A further object of the invention resides in the means allowing universal applicability of the device and method during wearer's ambulation and during stationary, upright and recumbent positions.

Another object of the invention lies in provision of structure for cosmetic acceptance and which results from the inconspicuous wearing or application of the device under every day attire.

A further object of the invention resides in the provision of structure and method which are efficient in operation and of a minimum number of parts and method steps. The structure is light in weight, strong and durable in use, economical to manufacture, easy to apply or operate, and capable of easy application and adjustment by the patient himself or herself.

Furthermore, a most significant object of the present invention lies in its therapeutic potential for restoring meaningful function in the hemiparetic upper limb. This particular application merits further elaboration. One of the most critical factors that prevents retraining of the arm and hand for function in stroke patients is the subluxation and instability at the shoulder joint which occurs in a very large percentage of patients. This subluxation, frequently causing pain, limits the attempt at retraining the patient for voluntary isolated movements. An attempted movement triggers off spasticity predominantly in the antigravity muscles and causes the pathological synergy response consisting of flexion at the elbow and internal rotation and retraction of the arm.

On the other hand, it is a fact that such patients given manual support under the elbow by the therapist are often capable of breaking out of the pathological synergy response and are able to demonstrate isolated voluntary movements. This supportive positioning of the arm is intended to temporarily reduce shoulder subluxation and decrease adduction and internal rotation of the arm.

Under the present invention, there are means to position the upper extremity in the same desirable manner or position for extended time, thus allowing the patient frequent exercise periods throughout the day. Such exercises may in time cause sizable decrease of subluxation or even its complete reduction. But during its persistence, the stability of the shoulder joint can be maintained by the present invention. While such stability of the shoulder joint can be adjusted from time to time as needed, the present invention allows freedom of movements of the elbow, wrist and finger joints at all such times. The recovery of function is often related to the duration of the repetitive self-induced and actively carried out movements which is made possible by the application of the present invention.

These objects and other ends and advantages of the invention will hereinafter appear in the progress of the disclosure and as pointed out in the appended claims.

DRAWINGS OF PREFERRED EMBODIMENT

In the accompanying drawings showing a preferred form of the invention:

FIG. 1 is a front view of wearer showing the device as attached and as it appears prior to any adjustment;

FIG. 2 is a view similar to FIG. 1 but showing the capacity of the rod element of the device to be pivoted to a desired and adjusted and locked spatial position for carrying wearer's or patient's arm as seen in phantom;

FIG. 5 is an enlarged view of the device as worn by the patient substantially as shown in FIG. 3 with parts being shown in section;

FIGS. 6 and 7 are each enlarged and partial views in section of the ball and socket joint and of the ball actuating rod of the device, said views showing respectively locked and unlocked condition of the joint;

FIG. 8 is an exploded view in perspective of the body attaching plate for anchorage of the device including the ball and socket joint adapted to be connected thereto;

FIG. 9 is an exploded view in perspective of the ball and socket joint parts and of the ball actuating rod;

Figure 3:
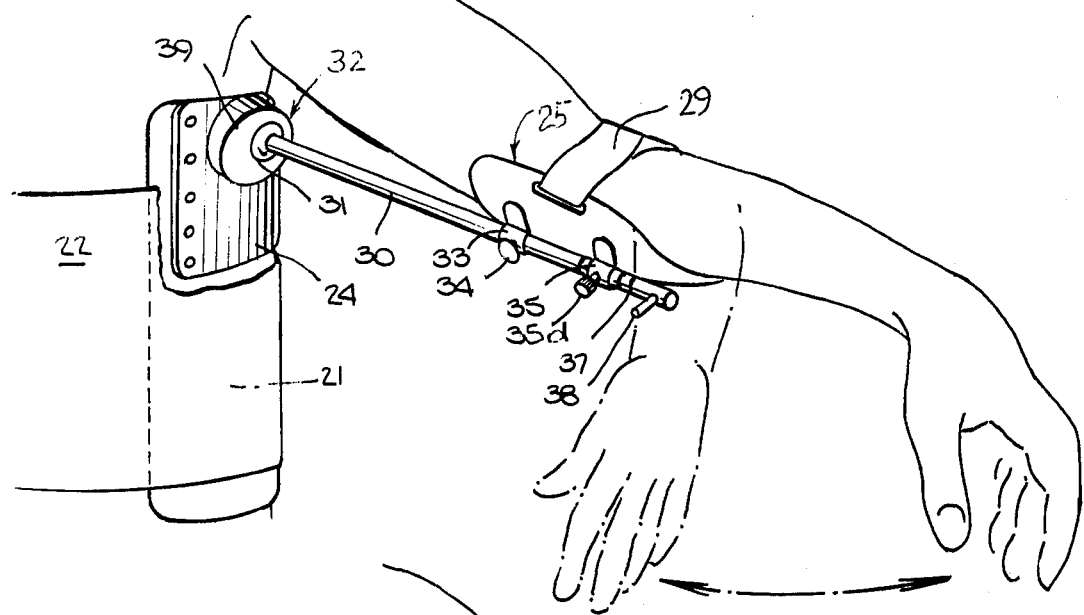
FIG. 3 is a view similar to FIG. 2 but showing the rod in locked adjusted position, also showing the trough in locked adjusted position as strapped to the patient's arm, a downward flexion of forearm of patient being illustrated in phantom.

FIGS. 10, 11 and 12 respectively are views in perspective showing disassembled portions of the device, namely; the body attaching plate having the ball and socket joint connected thereto; the actuating rod; and the elbow support or trough.

DESCRIPTION OF PREFERRED EMBODIMENT

The orthotic device with method involved in accordance with the preferred form of the invention is comprised of three novel and improved systemic structures and procedures, and a novel and improved combination thereof. System A involves attachment of the device to the human body; System B involves provision for effectuating stability and maintaining same during mobility of the human arm (or simultaneous stability and mobility); System C relates to provision of a novel and artificial ball and socket joint interposed between the body and the arm.

System A, Attachment to Body

As seen in FIGS. 1, 2, 3 and 4, the orthotic device, generally indicated by numeral 20, and for support is pivotally anchored to the upper portion of a rigid, retaining plate or standard 21 and curved as shown. Plate 21 conforms in contour to the lateral aspects of the chest area of the wearer by being individually fitted. To functionally and appropriately secure plate 21 to the body, a chest-encircling band 22 is provided to pocket plate 21 and anchor same to chest area of the body. As best seen in FIG. 8, and when plate 21 is formed of material such as a pressure-resisting polyvinyl chloride plastic or the like, a pair of shape-conforming rear and front plates 23 and 24 of suitable reinforcing material such as metal, alloy or plastic are applied at the upper portion of plate 21. Band 22 may be comprised of a strip of reinforced plastic webbing having Velcro (®) connecting terminals for adjustability. Plate 21, having a protective padding 21a on the rear side, is adapted to be forcibly inserted inside the adjusted and snug-fitting band 22 up to socket housing 39 as a stop, and between the arm and the lateral chest area of the body, as indicated in the drawings for supporting mounting of the device on the body.

System B-1, Stability and Mobility in General

A condensed summary of structure, application, adjustability mode of operation, and process involved of the device for affording both simultaneous and independent stability and mobility to the malfunctioning arm is now set forth to better understand the disclosure herein at this time.

Thus, elbow support or trough 25 has an opening for partial passage of the olecranon process to allow for full elbow flexion, full forearm pronation, and supination as well as for functional forearm extension. An attachment band 29 secures the trough to the wearer's arm. Trough 25 is slideably and rotatably connected to a rod 30 and has positional adjustment controls with respect to rod 30 and has positional adjustment controls with respect to and for fixation of the trough to the rod. The proximal end of rod 30 is pivotally connected to plate 21 through the intervention of an artificial ball and socket joint indicated generally by numeral 32 and adapted to be disposed below the wearer's shoulder joint and between the body and the arm. Means are provided to lock rod 30 into the desired pivoted position afforded by the ball and socket joint. Said ball and socket joint provides for the malfunctioning arm a functional and adequate range of spatial movement so as to parallel, replace or augment the malfunctioning human shoulder joint.

Trough 25, when in arm-unattached position and free of controls 34 and 36, when rod 30 is freely pivotal as shown in FIG. 1, is snugly fitted to the elbow joint of the wearer and band 29 is attached to the arm. Rod 30 is thereupon locked or fixed in any comfortable and desirable arm position of the wearer or patient. Trough 25 is then adjusted for support and exertion of pressure against the elbow in a proximal direction, and the controls activated to fix such pressurized position of the trough on rod 30. In this manner, stability of the arm is effected for the stated and comfortable and desirable arm position of the patient. It is in this stabilized arm condition that the patient or wearer has the above stated freedom of full elbow flexion, full forearm pronation and supination, as well as adequate and functional forearm extension.

Figure 4:
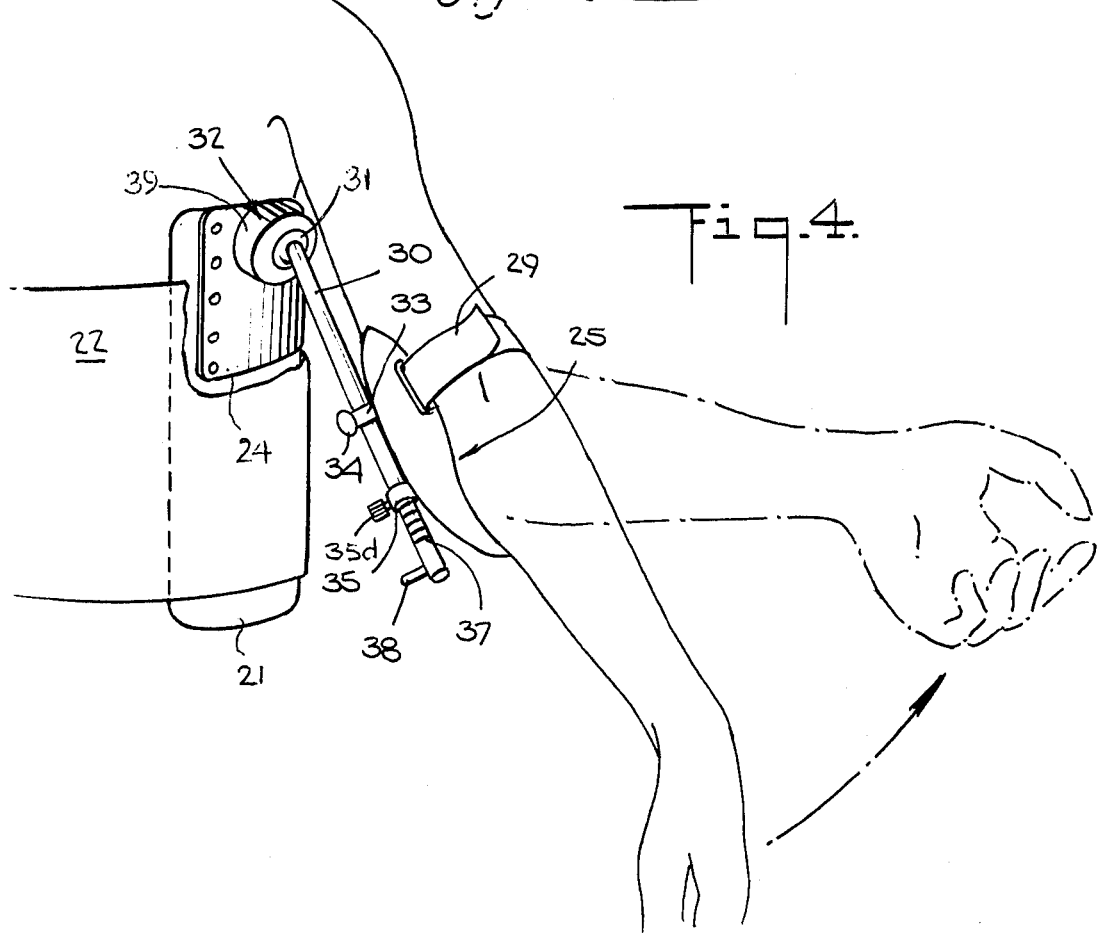
FIG. 4 is a view similar to FIG. 3 wherein the device is locked for a relatively adducted arm position, and also showing an upward flexion of forearm in phantom.

To effectuate change of arm position and at the same time retain arm stabilization, control 34 is deactivated to permit unlocking of rod 30 by rotation thereof at handle 38 at the rod distal end. The rod is then moved pivotally to desired functional arm position and then locked. At this time, control 36, if necessary, may be readjusted for elbow pressure, and control 34 activated for fixation of trough position. Fixed arm positions are illustrated in FIGS. 3 and 4.

System B-2, Stability and Mobility in Detail

More specifically and with respect to the stabilizing aspects of the device, the trough or elbow support element 25 is moldably or otherwise formed from any suitably hard, inert, and pressure-resisting plastic such as of the aforestated polyvinyl chloride or other composition having required characteristics. The trough is accurately formed as a mold from the elbow joint of each individual potential wearer, and while the malfunctioning limb is in about 150 degree extension at the elbow joint. An opening 28 to permit partial passage therethrough of the olecranon process is provided for and preferably in the process of trough formation. A soft padding or lining 25a of any suitable material is provided for comfort and protection of the wearer.

Accuracy of fit of the elbow support 25 is important. Opening perimetric edge 28a should supportingly engage substantially the full perimetric edge of the olecranon process at the base of its projection through said opening, while the humeral lateral and medial epicondyles are also engaged by adjacent parts of the trough 25. In this manner, support and appropriate pressure applied to the elbow by the trough will be transmitted to wearer's arm axially to correct subluxation of the shoulder joint as by forcing the humeral head into functioning and proper position with its socket (glenoid fossa). It is under such circumstances that full elbow flexion, full pronation and suppination of the forearm as well as functional extension of the forearm becomes possible. Absent such fit, downward sliding of wearer's arm as well as rotation thereof may take place thereby vitiating the trough function.

As best seen in FIG. 12, trough 25 as formed has an arm wing portion 26 to engaginly support part of the arm of the wearer, and has a forearm wing portion 27 to engagingly support part of the forearm, both portions being on opposite sides of opening 28. Attached to arm wing 26 is the aforementioned encircling band 29 adapted to secure trough 25 to the arm of the wearer, and which as shown has connectable ends provided with Velcro ® closure means for adjustability.

Trough 25 is adapted to be slideably and rotably attached to rod 30 to assure an adjustable and a laterally outer and adjacent position with respect thereto as best seen in FIG. 1. Such attachment is provided as by means of a pair of trough guides, one being indicated generally by numeral 33 and herein designated as the "proximal guide," and the other being generally indicated by numeral 35 and herein designated as the "distal guide."

As best seen in FIG. 5, rod 30 is preferably of metal such as aluminum, steel, alloy, or plastic, and is about one-half inch in diameter to sustain the imposition of limb load, and is of a length dependent on the anatomical measurements of the patient. Proximal guide 33 is preferably formed of a suitable material as above, and has an attaching bracket 33a carrying a block 33b also having a cylindrical bore 33c. Guides 33 and 35 are spaced in an alignment parallel with the trough longitudinal axis, and are suitably secured to and project from the outer face of the inner side wall of trough arm wing 26, thereby making provision for said aligned bores to engage rod 30 slideably and rotably.

Proximal guide 33, functioning to provide stability of trough 25 in any desired position has locking means for such purpose. Thus, a knurled and steel thumb screw 34 (about 10/32 inch) is used and which as shown is adapted to impinge against rod 30 by penetrating the bore 33c of block 33b.

Distalguide 35 like proximal guide 33 has an attaching bracket 35a carrying a depending bored block 35b for passage of rod 30 therethrough. Said block further is provided with a lower housing 35c which is adapted to mount a spring-urged retractable pin 36 having a pull knob 35d. Pin 36 is adapted to penetrate block 35b and fit within and rotably engage one of the preselected grooves on rod 30 to establish the longitudinal position of guide 35 with respect to rod 30. As above stated, the distal guide 35 functions to provide pressure-exerting support to the elbow as by pushing the humeral head in its socket (glenoid fossa) for joint stabilization.

Thus, the distal and proximal guides 35 and 33 afford the needed system of controls which can be operated manually by the patient. Said controls adjust the relationship between trough 25 and rod 30 longitudinally and rotably in space.

As best seen in FIGS. 5, 10 and 11, rod 30 at its proximal end is adapted to be connected to base plate 21 by the intervention of ball and socket joint 32, said joint being anchored to the plate adjacent to and intermediate the upper transverse edge. Rod 30 serves as the mounting means for the trough 25 and at its distal area provides the base for a plurality of grooves 37. A handle 38 at the distal end of the rod 30, shown in the form of a cross pin, is adapted to provide necessary leverage for rod rotation to control the locking and releasing of ball and socket joint 32 as will appear hereinafter.

Grooves 37 are circular and commence about one inch above handle 38 and run proximally for about two inches along rod 30. Said grooves are about ¼ inch apart, are about 1/16 inch deep and about 1/16 inch wide, all as best seen in FIG. 5. Retractable spring-controlled steel pin 36 of distal guide 35 is adapted to fit into one of the appropriately selected grooves 37 in order to provide the necessary pressure against the elbow. In this connection, it is to be observed that the spring for pin 36 is preferably soft to enable easy retraction by pull knob 35d from the grooves for change of groove positions. Whatever groove is selected by pin engagement provides the necessary pressure against the elbow for transfer to the patient's arm axially to assure the stability of the humeral head in the glenoid cavity.

System C, Artificial Ball and Socket Joint

The artificial ball and socket joint adapted to be interposed between the body and the arm of the patient performs in a manner paralleling the function of the human shoulder joint; whereas stability and mobility of the human arm are the result of forces exerted by a multitude of muscles, under the instant invention stability and mobility are the result of manually operated and adjusted controls of external structures.

Ball and socket joint 32 as best seen in FIGS. 8 and 9 includes ball component 31, preferably a steel ball ⅞ inch in diameter. Said ball is actuatable by rod 30 and is operative in a socket generally indicated by numeral 40. A housing 39 for said ball 31 and socket 40 is adapted to be attached to the base plate 21 for anchorage.

It is understood that the specifications herein disclosed of the joint are for a patient of average weight and size, and for a selected operational range of arm movement in space adequate for functional use of the malfunctioning arm. Such operational range is subject to variation, but as disclosed herein, is approximately as follows: an abduction and forward flexion in excess of 90 degrees; an adduction (negative) of minus 20 degrees; and an extension limited to 5 degrees.

Within said selected or other chosen operational range of spatial arm movement, changes and variations in assembly, size, strength and materials of parts of the joint will depend upon the anatomy and age of the patient, and the variability and severity of particular clinical signs and symptoms of the individual.

Accordingly, under the above specified operational range of arm spatial movement and for the patient of average weight and size, the artificial ball and socket joint is comprised of a stainless steel ball 31, and which is ⅞ inch in diameter and actuatable for movement in a socket 40 by the rod 30. Rod 30 is ½ inch in diameter, about 16 inches in length and of aluminum or other metallic or non-metallic composition suitable for its function. Housing 39 containing socket 40 is also of any suitable composition as of aluminum, steel, alloy or non-metallic material and is adapted to be anchored along the upper end of the vertical axis of base plate 21, and about ¼ inch below the base plate upper edge as best seen in FIG. 5.

Socket 40 is preferably created by the use of a ⅞ inch diameter ball-end mill drill applied at right angles to housing rear wall 39b. The diameter of the cylindrical recess portion thus formed corresponds to the diameter of ball 31 adapted to be inserted therein. Cylindrical recess 39d formed by said application terminates short of housing front wall 39a and becomes coextensive with spherical socket section 39e, the latter being of a 7/16 inch radius taken on the socket axis 3/16 of an inch inwardly of front housing wall 39a. Said spherical socket section is conventionally formed by the ⅞ inch diameter ball-end mill and cuts housing front wall 39a at the circular opening 39f as best seen in FIGS. 6, 7 and 8. Opening 39f has a lesser diameter than ball 31 permitting the latter to project therebeyond, the ball being restrained by the peripheral skirt or ballbearing overhang portion afforded by said section 39e.

To maintain steel ball 31 within socket 40, a cylindrical plug 41 of same diameter as cylindrical recess 39d is inserted within said recess, as best illustrated in FIG. 9 for engagement with the rear ball portion. Front wall 42 of plug 41 is in the form of a semi-spherical socket of 7/16 inch radius for ball engagement, while the plug rear end has a reduced portion 43 forming a circular shoulder or rear wall 43a therewith and therebelow.

Shoulder 43a is adapted to be peripherally engaged by a split steel retaining ring 44 of larger diameter than plug 41. Ring 44 is radially, inwardly and resiliently flexible, and has inturned and opposing end lugs 44a, each provided with pinch-tool engaging elements such as orifices 44b to reduce the diameter thereof for introduction into housing recess 39d and onto shoulder 43a.

Suitable provision is made to secure plug 41 to housing 39 and at the same time to maintain the steel ball 31 within the socket 40. Thus, coextensive with the shoulder floor is an internal circular groove 45 in recess 39d and which is adapted to receive a peripheral part of ring 44 upon being sprung by release of the pinch tool from lugs 44a. Thus, the plug is suitably secured to housing 39 and urges ball 31 against the restraining socket section 39e adjacent front wall 39a of housing 39, all as best seen in FIGS. 7 and 8. Friction in movement between ball 31 and its socket-bearing surfaces is maintained at a minimum and depends on position of shoulder 43a and coextensive groove 45 in cylindrical recess 39d relative to ball 31.

As best seen in FIGS. 9 and 11, rod 30 at the proximal end is reduced to a diameter of ⅜ inch for threading into the center ⅜ inch bore of ball 31 from the exposed ball end. Bore of ball 31 is internally threaded as at 46 at the rate of 32 threads to the inch while the rod portion at reduced diameter is correspondingly externally threaded as at 47. The proximal end of rod 30 is preferably rounded at a 7/16 inch radius as at 48.

Thus, turn of the rod 30 after fully and threadedly engaging ball 31 is adapted to engage plug socket surface 42 thereby locking ball in any desired stationary position within its bearing socket. The turn of rod 30 is accomplished by rotation of handle 38 at the rod distal end. The minimum friction present between ball 31 and its socket prevents the ball from rotating while rod 30 is being threaded for insertion therein, for locking and unlocking, and for removal.

Angles of anchorage of housing 39 to base plate 21 contribute to effect the operational and functional range of spatial arm or rod movement under the range herein specified. Thus housing 39 is applied to base plate 21 along the vertical axis at the upper end and about ¼ inch below the top transverse edge as heretofore stated. Attachment is by way of engagement of a lower 45 degree offset portion 39c extending from rear wall 39b as best seen in FIG. 9. A second offset at about 45 degrees or less shown in phantom at 39c' and extending from one end of offset portion 39c may be further provided for controlling the angulation or tilting of housing 39 with respect to base plate 21 as seen in FIGS. 1–4 and 8. So that when rod 30 is in a perpendicular position with respect to housing front wall 39a, the position of rod 30 is at about a 45 degree angle with respect to base plate 21. As best seen in FIG. 8, housing 39 is attached to plate 21 as by screw-attaching means 50.

With respect to the disclosed dimensioning and shaping of parts as herein already described, it may be mentioned that as shown, housing 39 is substantially in the form of a cylindrical section the front face of which is 1¾ inches in diameter and the thickness ⅜ inch. With respect to plug 41, same is ⅞ inch in diameter and reduced to 9/16 for formation of shoulder 43a.

In operation of the device, it is to be observed that by unlocking rod 30, ball and socket joint 32 becomes operational for any desired spatial position, while the support of the elbow and axially directed pressure thereon keep the human arm joint in proper alignment.

Further Features

The device of the invention is applicable to a variety of conditions of malfunction.

Thus, if the shoulder joint requires no stabilization, but another dysfunction is present which involves the arm, the no axial pressure on the arm is necessary. For movement and adjustment of the arm under such circumstances, a groove 37 is first chosen that exerts no axial pressure, then thumb screw 34 is loosened. At this time, rod 30 may be moved in any direction; but when at a desired position, the rod is fixed by the thumb-screw tightening. In this way, the axial pressure function to the arm is inactivated for stabilization, and the function for mobility alone is utilized.

The device is further applicable to conditions relating to malfunctions affecting pronation and supination of the forearm. Such movements are attainable by rotational movement of the trough 25 about rod 30 upon loosening of thumb-screw 34, and thereafter tightening said thumb-screw at any desired functional position. Moreover, in hemiplegic cases, the patient himself or herself may apply and adjust the device.

Particularly in stroke patients, while subluxation may be common, there are times that the pull of certain muscles keeps the humeral head in aligned position in the glenoid cavity (fossa). In such cases, no axial pressure to the arm is needed, and the main application of the device is to position the arm in space to prevent involuntary arm adduction. If the arm is supported, then patient can operate the forearm functionally; whereas in absence of such support and when the arm is in adduction and in engagement with the body, such operation is not feasible.

Webbing or encircling band 22 used in the device herein is further applicable as a mounting for and compressing means on resilient and wedge-shaped pads to support the scapula in such a way as to prevent or minimize undesirable rotation occurring in some injuries to the central and peripheral nervous systems. In stroke patients, paresis and spasticity of certain muscles adapted to anchor the scapula cause a change in the relationship wherein the straight medial edge at the lower triangular end is rotated or shifted medially. This permits the forces of gravity to extend or pull the arm out of its socket, thereby adding to the subluxation at the gleno-humeral joint.

For such mounting and compressing function, band 22 encircling and peripherally bearing pressure against the chest wall can serve as an inner pocket for securing and compressing a wedge-shaped pad against the straight medial edge of the lower triangular end of the scapula to exert lateral pressure toward derotation of the scapula when needed. Such lateral pressure and derotation partially restores the integrity of the scapulohumeral joint, is an aid in use of the device of the invention and is helpful in an exercise program.

The device under the invention herein has additional production and consumer advantages in that substitution, replacement, and interchange of many parts, as herein described in modular form, are feasible.

Conclusion

It is understood that the invention as embodied in the preferred form and in the procedure and process involved has been mainly directed (although not exclusively) to its application to the variety of neurological diseases where stability and mobility at the shoulder joint are absent or diminished. For in health, the stability and mobility of the human arm is possible because of coordinated muscular activity acting at the level of the shoulder joint.

It is further understood that minor changes and variations in size, shape, location, composition, assembly and combination of parts involved in the invention, together with minor changes and variations in procedure and process steps also involved may all be resorted to without departing from the spirit of the invention and the scope of the appended claims.

I claim:

1. An orthotic device for the human upper limb comprising:
   (a) a standard to support the device, and attaching means to secure said standard between the arm and body of the patient at the chest area;
   (b) a rod member and connecting means operative between the rod at its proximal end and said standard, said connecting means being adapted to position the rod along a desired, fixed, and functional spatial arm position;
   (c) elbow supporting means attachable to the arm of the patient and being rotatably and slideably mounted on said rod, said elbow supporting means having an intermediate opening for support and projection of patient's olecranon process;
   (d) first control means between said rod and elbow supporting means to adjust and releasably lock the adjusted longitudinal position of said elbow supporting means on said rod when applied to the patient whereby to control needed pressure application to the projecting portion of said olecranon process for stabilizing a malfunctioning arm by transmission of pressure proximally to and axially of the arm to provide for and render full elbow flexion, full forearm supination and pronation, and functional forearm extension in said locked longitudinal position; and (e) second control means between said rod and elbow supporting means to releasably lock said adjusted and locked longitudinal position of the elbow supporting means on said rod against rotary movement.

2. An orthotic device as in claim 1 wherein said standard comprises a plate contoured to patient's chest area below and adjacent the armpit and adapted to be functionally secured thereto; and wherein said attaching means for the said standard comprises a removable and adjustable chest-encircling and resilient webbing element adapted to be applied across the patient's chest area under comfortable and functional tension and over said plate for plate securement.

3. An orthotic device for the human upper limb comprising:
(a) a standard to support the device, and attaching means to secure said standard between the arm and body of the patient at the chest area;
(b) a rod member adapted to carry at least one supporting pad for and attachable to upper limb parts, said rod being operatively connected at its proximal end to said standard;
(c) a housing anchored to said standard and containing ball and socket joints means, the housing having an opening in the front wall for projection of part of said ball;
(d) connecting means between the proximal end area of said rod and the said ball to enable the rod to assume an adequate, operational, and predetermined range of spatial, functional and releasable fixed arm positions, whereby said ball and socket joint means serves to parallel, augment and replace the human shoulder joint for arm mobility.

4. An orthotic device as in claim 3 wherein said standard comprises a plate member contoured to patient's lateral chest area below and adjacent the arm pit and adapted to be functionally secured thereto, said housing being anchored to said plate member; and wherein said attaching means for the said standard comprises a removable and adjustable chest-encircling and resilient webbing element adapted to be applied across the patient's chest area under comfortable and functional tension and over said plate for securement thereof.

5. An orthotic device for the human upper limb comprising:
(a) a standard to support the device, and attaching means to secure said standard between the arm and body of the patient at the chest area;
(b) a rod member adapted to carry an elbow support which is attachable to the arm of the patient, said rod member at the proximal end being operatively connected to the said standard, said elbow support being rotatbly and slideably mounted on said rod and having an intermediate opening for support and projection of patient's olecranon process;
(c) first control means between said rod and elbow support to adjust and releasably lock the adjusted longitudinal position of said elbow support on said rod when applied to the patient whereby to control needed pressure application to the projecting portion of said olecranon process for stabilizing a malfunctioning arm by transmission of pressure proximally to and axially of the arm to provide for and render full elbow flexion, full forearm supination and pronation, and functional forearm extension in said locked longitudinal position;
(d) second control means between said rod and elbow support to releasably lock said adjusted and locked longitudinal position of the elbow support on said rod against rotary movement;
(e) a housing anchored to said standard and containing ball and socket joint means, the housing having an opening in the front wall for projection of part of said ball; and
(f) connecting means between the proximal end area of said rod and the said ball to enable the rod to assume an adequate, operational, and predetermined range of spatial, functional and releasably fixed arm positions, whereby said ball and socket joint serves to parallel, augment and replace the human shoulder joint for arm mobility while at the same time maintaining arm stability.

6. An orthotic device as in claim 5 wherein said standard comprises a plate member contoured to patient's lateral chest area below and adjacent the armpit and adapted to be functionally secured thereto, said housing being anchored to said plate member; and wherein said attaching means for the said standard comprises a removable and adjustable chest-encircling and resilient webbing element adapted to be applied across the patient's chest area under comfortable and functional tension and over said plate for securement thereof.

7. In a process for stabilization of a malfunctioning upper limb wherein is provided an orthotic device having a rod attached at its proximal end to a standard secured under the armpit, said rod being adapted to assume any operational, adequate and functional position in space corresponding to that of the human arm, said rod carrying an adjustable elbow support attached to the arm, said support having an intermediate opening for the olecranon process, the improvement comprising:
(a) fitting and applying pressure proximally to the elbow support on and against the patient's elbow and projecting olecranon process for transmission to and axially of the arm for arm stabilization, and simultaneously provide for and render full elbow flexion, full forearm supination and pronation, and functional forearm extension for any of said rod positions; and
(b) releasably locking said adjusted and pressure applied position of the elbow support by means of rotary and longitudinal controls between said elbow support and said rod.

8. In a process for mobilizing a malfunctioning upper limb wherein is provided an orthotic device having a rod operatively attached at its proximal end below the armpit to a standard, said standard being secured to the body of the patient for assuming operational and adequate functional positions in space corresponding to those of the human arm, said rod carrying at least one adjustable support for an upper limb part, said support being attachable to patient's arm, the improvement comprising the steps of:
(a) introducing ball and socket joint means between the said rod and said standard to parallel, augment and replace the human shoulder joint function; and (b) releasably locking any desired spatial position of the rod by means of controls between the rod and said joint means.

9. In orthosis, the process for stabilizing and mobilizing a malfunctioning upper limb and maintaining the stabilized condition during arm mobility, and wherein is provided an orthotic device having a rod attached at its proximal end to the ball of a ball and socket releasably lockable joint means, said joint means being attached to a standard secured below the patient's armpit, said rod carrying an adjustable elbow support attachable to the arm and having an intermediate opening for receiving the olecranon process, the improvement comprising the steps of:

(a) fitting and applying pressure proximally to the elbow support on and against the patient's elbow and projecting olecranon process for transmission of said pressure to and axially of the arm for stabilizing the arm and simultaneously to allow for and render full elbow flexion, full forearm supination and pronation, and functional forearm extension for any of said rod positions when in releasably locked condition;

(b) rleasably locking said adjusted and pressure-applied position of the elbow support by means of rotary and longitudinal controls between said elbow support and said rod; and (c) changing and releasably locking the changed rod position while maintaining the stabilized condition of the arm by manipulating respectively controls between the elbow support and the rod, and between the rod and the ball and socket joint means.

10. In orthosis, the process as set forth in claim 9 wherein the improvement includes additional steps of utilizing a removable and adjustable chest-encircling and resilient webbing element as means to secure the device to the body, and which element is adapted to be applied across the lateral part of the chest area of the patient and below the armpit, and further utilizing a contoured plate fitted to the patient at the lateral chest area and below the armpit in place of said standard, and to which plate the ball and socket joint means is attached, said webbing element being adapted to secure said plate to the patient's body at said lateral chest area and below the armpit.

* * * * *